United States Patent [19]

Miyauchi et al.

[11] Patent Number: 5,736,406
[45] Date of Patent: Apr. 7, 1998

[54] METHOD OF DETERMINING THE AMOUNT OF CHOLESTEROL IN A HIGH-DENSITY LIPOPROTEIN

[75] Inventors: Kazuhito Miyauchi, Shizuoka; Norihiko Kayahara, Kawasaki; Toshio Tatano, Numazu; Eiko Shutoh, Ohita; Hiroyuki Sugiuchi; Tetsumi Irie, both of Kumamoto; Kaneto Uekama, Kumamoto; Susumu Ohsawa, Yotsukaido, all of Japan

[73] Assignee: Kyowa Medex Co., Ltd., Tokyo, Japan

[21] Appl. No.: 545,725

[22] PCT Filed: Mar. 8, 1995

[86] PCT No.: PCT/JP95/00379

§ 371 Date: Nov. 2, 1995

§ 102(e) Date: Nov. 2, 1995

[87] PCT Pub. No.: WO95/24647

PCT Pub. Date: Sep. 14, 1995

[30] Foreign Application Priority Data

Mar. 8, 1994 [JP] Japan .................. 6-37329
Apr. 27, 1994 [JP] Japan .................. 6-89431

[51] Int. Cl.$^6$ .................................................. G01N 33/50
[52] U.S. Cl. .............................. 436/71; 436/166; 435/11; 435/19
[58] Field of Search .................. 436/71, 166; 435/11, 435/28, 19

[56] References Cited

U.S. PATENT DOCUMENTS

| | | | |
|---|---|---|---|
| 4,647,532 | 3/1987 | Watanabe et al. | 435/28 |
| 4,778,753 | 10/1988 | Yamanishi et al. | 435/10 |
| 4,851,335 | 7/1989 | Kerscher et al. | 435/11 |
| 4,892,815 | 1/1990 | Kerscher et al. | 435/7 |

FOREIGN PATENT DOCUMENTS

| | | |
|---|---|---|
| 62-69999 | 3/1987 | Japan . |
| 63-126498 | 5/1988 | Japan . |
| 1-179688 | 7/1989 | Japan . |
| 1-273585 | 11/1989 | Japan . |
| 6-242110 | 9/1994 | Japan . |

OTHER PUBLICATIONS

Original by Izumi Kanai, Edited by Masamitsu Kanai, "A Summary of Clinical Test" (No. 29 Revised Edition) Jun. 30, 1983 (30.06.83) pp. 471–474.

*Primary Examiner*—Jeffrey Snay

[57] ABSTRACT

Provided are a method of determining the amount of cholesterol in high-density lipoprotein (HDL), which comprises measuring the amount of cholesterol in low-density lipoprotein (LDL), very-low-density lipoprotein (VLDL) and chylomicron (CM) in a sample in the presence of a sugar compound and/or a protein solubilizing agent, and calculating the difference between the amount of cholesterol in LDL, VLDL and CM and the total amount of cholesterol in the sample, and a method of determining the amount of cholesterol in HDL, which comprises measuring the amount of cholesterol in HDL in a sample in the presence of a sugar compound and/or a protein solubilizing agent.

8 Claims, 2 Drawing Sheets

METHOD OF DETERMINING THE AMOUNT OF CHOLESTEROL IN A HIGH-DENSITY LIPOPROTEIN

TECHNICAL FIELD

The present invention relates to a method of determining the amount of cholesterol in a high-density lipoprotein (HDL) [hereinafter referred to as "HDL cholesterol"]. HDL is important in lipid metabolism in the field of clinical diagnosis.

BACKGROUND ART

It is known that HDL is related to the removal of cholesterol accumulated in cells for receiving cholesterol from tissues including arterial walls, that HDL is a negative risk factor of various types of arteriosclerosis such as coronary arteriosclerosis, and that HDL level in blood is an index useful for the precognition of arteriosclerosis. The conventional method of determining the amount of HDL cholesterol consists of two steps, a fractionation step and a step of determining the amount of cholesterol. Examples of the fractionation include an ultracentrifugation method, an immunochemical method, an electrophoretic method and a precipitation method. In the ultracentrifugation method, HDL is separated through specific gravity using an ultracentrifuge to determine the amount of HDL cholesterol. However, this method is defective in precision in determination, complexity and economical efficiency. The immunochemical method includes an immunoelectrophoretic method, a single radial immunodiffusion (SRID) method, and an Ouchterlony diffusion method. However, these methods are defective in that an apoprotein is recognized but a lipoprotein is not exactly recognized. In the electrophoretic method, a cellulose acetate film or an agarose gel is separated as a support, and the amount of cholesterol is enzymatically determined. This method is defective in simplicity and economical efficiency. In the precipitation method, polyethylene glycol or a polyanion such as heparin, phosphotungstic acid and dextran sulfuric acid, and a divalent cation are bound to an apoprotein B, which is present on surfaces of low-density lipoprotein (LDL), very-low-density lipoprotein (VLDL) and chylomicron (CM) to form an insoluble precipitate, and this insoluble precipitate is removed by centrifugation to determine the amount of HDL cholesterol in the supernatant (Summary of Clinical Investigation Method, 29th edition, Kanai I., Kanehara Shuppan, p. 471, 1983). This method is the simplest. However, this method is not suitable in case of using an autoanalyzer which is often used in measuring a large number of specimens, for rapid measurement and in clinical investigation, since this method involves centrifugation step by a centrifuge. Further, in the fractionation, a mannual error tends to occur, for example, when the amount of the HDL fraction separated is determined using a measuring pipet. Thus, the complexity of the determination of the amount of HDL cholesterol lies in the fractionation procedure. However, if a serum specimen is directly added to a reagent containing a cholesterol esterase and a cholesterol oxidase without fractionating HDL, this method is not different from a system of determining the total amount of cholesterol, and the amount of HDL cholesterol cannot be specifically determined by this method. Japanese Published Unexamined Patent Application No. 126,498/1988 describes that a cholic acid is added to increase the specificity. However, in this prior art method, not only HDL but also LDL, VLDL and the like gradually react, and it is difficult to obtain a clear terminal point of the reaction, and thus, the specificity of HDL by the use of this prior art method is not satisfactory.

DISCLOSURE OF THE INVENTION

The present inventors have determined the amount of cholesterol in lipoproteins such as HDL, LDL, VLDL and CM, each of which has been fractionated through ultracentrifugation, using a reagent containing a sugar compound and/or a protein solubilizing agent, and found that the reactivity of each of the lipoproteins with the reagent differs depending on the combination of the sugar compound and/or the protein solubilizing agent in the reagent, which leads to the difference in the reactivity of HDL cholesterol, LDL cholesterol, VLDL cholesterol and CM cholesterol. This finding has led to the completion of the present invention.

The present invention relates to a method of determining the amount of HDL cholesterol which comprises measuring the amount of cholesterol in LDL, VLDL and CM in a sample in the presence of a sugar compound and/or a protein solubilizing agent, and calculating the difference between the amount of cholesterol in LDL, VLDL and CM and the total amount of cholesterol in the sample.

The present invention further relates to a method of determining the amount of HDL cholesterol, which comprises measuring the amount of HDL cholesterol in a sample in the presence of a sugar compound and/or a protein solubilizing agent.

Preferable examples of the sugar compound include a compound represented by formula (I)

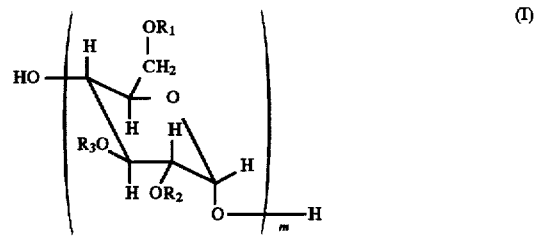

wherein $R_1$, $R_2$ and $R_3$ independently represent hydrogen, substituted or unsubstituted alkyl, substituted or unsubstituted alkanoyl, sulfo, —(glucosyl)$_p$—H (in which p is 1 or 2) or —(maltosyl)$_q$—H (in which q is 1 or 2), and m is an integer of 6 to 8, and a compound represented by formula (II)

$$(C_6H_{10}O_5)_n SO_3 R_4 \qquad (II)$$

wherein $R_4$ represents hydrogen or Na, and n is an integer of 5 to 2,000.

Preferable examples of the protein solubilizing agent in determining the amount of cholesterol in each of LDL, VLDL and CM in the sample include a compound represented by formula (III)

$$R_5(CH_2CH_2O)_a H(C_2H_4OOR_6)_b \qquad (III)$$

wherein a is an integer of 1 to 200, b is 0 or 1, $R_5$ represents $R_{14}$—X—O— (in which $R_{14}$ represents alkyl or alkenyl, and X represents a single bond or CO), or H—(CH$_2$CH$_2$O)$_c$—N(R$_{15}$)— (in which c is an integer of 1 to 200 and $R_{15}$ represents alkyl or alkenyl), and $R_6$ represents alkyl or alkenyl, a compound represented by formula (IV)

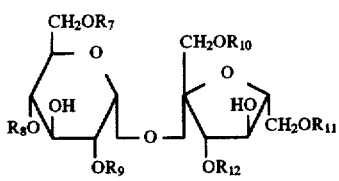

wherein $R_7$, $R_8$, $R_9$, $R_{10}$, $R_{11}$ and $R_{12}$ independently represent alkanoyl, and a compound represented by formula (V)

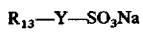

wherein $R_{13}$ represents alkyl or alkenyl, and Y represents

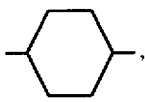

—O—, —CH($R_{16}$)— (in which $R_{16}$ represents alkyl or alkenyl), —CH$_2$CH(OH)(CH$_2$)$_d$— (in which d is an integer of 1 to 22), —CH=CH(CH$_2$)$_e$— (in which e is an integer of 1 to 22), —OCOCH(CH$_2$COOR$_{17}$)— (in which $R_{17}$ represents alkyl or alkenyl), or a mixture thereof.

Examples of the protein solubilizing agent in determining the amount of HDL cholesterol in the sample include a compound represented by formula (VI)

wherein $R_{18}$ represents alkyl or alkenyl, a compound represented by formula (VII)

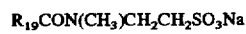

wherein $R_{19}$ represents alkyl or alkenyl, a compound represented by formula (VIII)

wherein f is an integer of 1 to 100, and $R_{20}$ represents alkyl, and a bile acid.

The compounds represented by formulae (I) to (VIII) will be hereinafter referred to as "compounds (I) to (VIII)".

In the definitions of the groups in formulae (I) to (VIII), the alkyl and the alkyl moiety of the alkanoyl mean a straight-chain or branched alkyl group having 1 to 22 carbon atoms such as methyl, ethyl, propyl, isopropyl, butyl, isobutyl, sec-butyl, tert-butyl, pentyl, isopentyl, neopentyl, hexyl, heptyl, decyl, pentadecyl, icosanyl and docosanyl. The alkenyl means an alkenyl group having 2 to 22 carbon atoms such as vinyl, propenyl, butenyl, pentenyl, hexenyl, heptenyl, decenyl, pentadecenyl, icosenyl and docosenyl.

Examples of the substituent of the substituted alkyl and the substituted alkanoyl include hydroxy, carboxy and sulfo.

Examples of the bile acid include a compound represented by formula (IX)

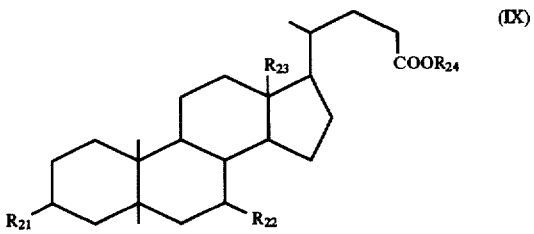

wherein $R_{21}$ and $R_{22}$ independently represent hydrogen, —OR$_{25}$ (in which $R_{25}$ represents hydrogen, sulfo or SO$_3$Na) or oxo, $R_{23}$ represents hydrogen or —OR$_{25}$ (in which $R_{25}$ is the same as defined above), and $R_{24}$ represents hydrogen, alkyl, alkenyl or metal.

Examples of the metal include an alkali metal such as sodium and potassium, and an alkaline earth metal such as magnesium and calcium. The alkyl and alkenyl are the same as defined above.

As the sugar compound, cyclodextrin derivatives are preferable among compounds (I) and (II), and methylated cyclodextrin is especially preferable. Examples thereof include α-cyclodextrin, β-cyclodextrin, γ-cyclodextrin, dimethyl-β-cyclodextrin, trimethy-β-cyclodextrin, hydroxyethyl-β-cyclodextrin, 2-hydroxypropyl-α-cyclodextrin, 2-hydroxypropyl-β-cyclodextrin, carboxymethyl-β-cyclodextrin, glycosyl-β-cyclodextrin, maltosyl-α-cyclodextrin, maltosyl-β-cyclodextrin, partially-methyl-β-cyclodextrin, α-cyclodextrin sulfate, and β-cyclodextrin sulfate.

As the protein solubilizing agent in determining the amount of cholesterol in LDL, VLDL and CM in the sample, nonionic and anionic surfactants are especially preferable among the surfactants such as compounds (III), (IV) and (V). Examples of the nonionic surfactant include polyoxyethylene lauryl ether, polyoxyethylene cetyl ether, polyoxyethylene stearyl ether, polyoxyethylene oleyl ether, polyoxyethylene behenyl ether, polyoxyethylene monolaurate, polyoxyethylene monostearate, polyoxyethylene monooleate, polyoxyethylene laurylamine, polyoxyethylene stearylamine and sucrose fatty acid ester. Examples of the anionic surfactant include sodium dodecylbenzenesulfonate, sodium n-dodecylbenzenesulfonate, sodium lauryl sulfonate, and higher alcohol sulfuric ester soda.

As the protein solubilizing agent for determining the amount of HDL cholesterol in the sample, cationic, anionic and nonionic surfactants and a bile acid salt are especially preferable among the surfactants such as compounds (VI), (VII) and (VIII) and the bile acid. Examples of the cationic surfactant include oxyethylene dodecylamine, polyoxyethylene dodecylamine and polyoxyethylene octadecylamine. Examples of the anionic surfactant include sodium cocoylmethyltaurate, sodium lauroylmethyltaurate, sodium myristoylmethyltaurate, sodium palmitoylmethyltaurate and sodium stealoylmethyltaurate. Examples of the nonionic surfactant include polyoxyethylene lauryl ether, polyoxyethylene cetyl ether, polyoxyethylene stearyl ether, polyoxyethylene oleyl ether and polyoxyethylene behenyl ether. Examples of the bile acid salt include sodium cholate, sodium deoxycholate, sodium chenodeoxycholate, sodium ursodeoxycholate, sodium lithocholate, sodium isochenodeoxycholate, sodium 7-oxolithocholate, sodium 12-oxolithocholate, sodium 12-oxochenodeoxycholate and sodium 7-oxodeoxycholate.

The present invention is characterized in the presence of the sugar compound and/or the protein solubilizing agent in the system of the reagent for determining the amount of cholesterol. The system of determining the amount of cholesterol follows a general method based on the following reaction principle, provided that the color substance and the measurement wavelength are not limited to those shown below.

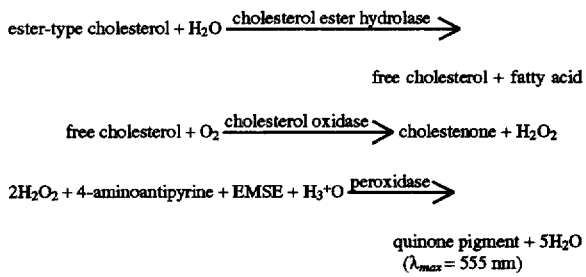

*EMSE: N-ethyl-N-(3-methylphenyl)-N'-succinylethylenediamine

Examples of the cholesterol ester hydrolase include commercial cholesterol esterase and commercial lipoprotein lipase which are derived from a microorganism or an animal having the ability to hydrolyze a cholesterol ester.

Examples of the cholesterol oxidase include commercial cholesterol oxidase which catalyzes the oxidation of cholesterol to form hydrogen peroxide and is derived from a microorganism.

In order to improve the specificity and the stability of the above-mentioned enzymes, the enzymes can be chemically modified by a group mainly composed of polyethylene glycol, a water-soluble oligosaccharide residue, a sulfopropyl group. An enzyme obtained by the gene manipulation can also be used.

The method of the present invention can be applied to a body fluid containing HDL, such as blood and urine.

The method of the present invention will be described hereinafter.

In conducting the method of the present invention, the solution of the sugar compound and/or the solution of the protein solubilizing agent are first prepared. The solution of the sugar compound is prepared by dissolving the sugar compound in a suitable buffer, for example, 50-mM tris-hydrochloride buffer (pH 7.4) such that the concentration of the sugar compound becomes, for example, 100 mM or less, preferably 3 to 80 mM at the time of the reaction. The sugar compound may be added to the reagent for determining the amount of cholesterol. The solution of the protein solubilizing agent is added to the reagent for determining the amount of cholesterol, and it is prepared such that the concentration of the protein solubilizing agent becomes, for example, 50 g/l or less, preferably 0.1 to 20 g/l at the time of the reaction. The reagent of the present invention is prepared from the solution of the sugar compound and/or the solution of the protein solubilizing agent containing the reagent for determining the amount of cholesterol, and maintained at 20° to 50° C., preferably 30° to 40° C. for approximately 5 minutes.

Then, the sample as such or the sample which has been diluted with water or a physiological saline solution is added to the above-mentioned reagent, and the reaction is conducted for 5 to 30 minutes. After the completion of the reaction, an absorbance of the reaction solution is measured at 500 to 600 nm, for example, at 555 nm to calculate the amount of cholesterol. In case that the amount of cholesterol in LDL, VLDL and CM in the sample has been measured, the total amount of cholesterol in the sample is separately measured, and the difference between the amount of cholesterol in LDL, VLDL and CM and the total amount of cholesterol in the sample is calculated to determine the amount of HDL cholesterol.

The following Test Examples show that the reactivity of each of HDL, LDL, VLDL and CM differs depending on the combination of the sugar compound and/or the protein solubilizing agent in the system of the reagent in determining the amount of cholesterol in each of the lipoproteins by the above-mentioned method.

Test Example 1

Using the fractions of HDL, LDL, VLDL and CM which had been fractionated from the serum by ultracentrifugation, the reactivity of each of the lipoproteins with the reagent was measured. In the reagent for determining the amount of cholesterol, 5 mM sugar compound and 5 g/l polyoxyethylene lauryl ether as the protein solubilizing agent were contained. The results are shown in Table 1.

TABLE 1

| Sugar compound | HDL | LDL | VLDL | CM |
|---|---|---|---|---|
| α-cyclodextrin | + | ++ | ++ | ++ |
| β-cyclodextrin | + | ++ | ++ | ++ |
| γ-cyclodextrin | + | ++ | ++ | ++ |
| dimethyl-β-cyclodextrin | − | +++ | +++ | +++ |
| trimethyl-β-cyclodextrin | − | +++ | +++ | +++ |
| hydroxyethyl-β-cyclodextrin | − | ++ | ++ | ++ |
| 2-hydroxypropyl-α-cyclodextrin | + | ++ | ++ | ++ |
| 2-hydroxypropyl-β-cyclodextrin | − | ++ | ++ | ++ |
| carboxymethyl-β-cyclodextrin | + | ++ | ++ | ++ |
| glucosyl-β-cyclodextrin | + | ++ | ++ | ++ |
| maltosyl-α-cyclodextrin | + | ++ | ++ | ++ |
| maltosyl-β-cyclodextrin | + | ++ | ++ | ++ |
| partially-methyl-β-cyclodextrin | + | ++ | ++ | ++ |
| α-cyclodextrin sulfate | + | ++ | ++ | ++ |
| β-cyclodextrin sulfate | + | ++ | ++ | ++ |

−, +, ++ and +++ indicate the reaction intensities, and the order of the intensities is − < + < ++ < +++.

When the sugar compound and the polyoxyethylene lauryl ether as the protein solubilizing agent are present in the reagent for determining the amount of cholesterol, the amount of HDL cholesterol can be indirectly determined from the amount of cholesterol in LDL, VLDL and CM.

Test Example 2

Using the fractions of HDL, LDL, VLDL and CM which had been fractionated from the serum by ultracentrifugation, the reactivity of each of the lipoproteins with the reagent was measured. In the reagent for determining the amount of cholesterol, 5 mM dimethyl-β-cyclodextrin as the sugar compound and 5 g/l protein solubilizing agent were contained. The results are shown in Table 2.

TABLE 2

| Protein solubilizing agent | HDL | LDL | VLDL | CM |
|---|---|---|---|---|
| polyoxyethylene lauryl ether | − | +++ | +++ | +++ |
| polyoxyethylene cetyl ether | + | +++ | +++ | +++ |
| polyoxyethylene stearyl ether | − | +++ | +++ | +++ |
| polyoxyethylene oleyl ether | + | +++ | +++ | +++ |
| polyoxyethylene behenyl ether | + | +++ | +++ | +++ |
| polyoxyethylene | − | +++ | +++ | +++ |

TABLE 2-continued

| Protein solubilizing agent | HDL | LDL | VLDL | CM |
|---|---|---|---|---|
| monolaurate | | | | |
| polyoxyethylene monostearate | − | +++ | +++ | +++ |
| polyoxyethylene monooleate | − | +++ | +++ | +++ |
| polyoxyethylene laurylamine | − | +++ | +++ | +++ |
| polyoxyethylene stearylamine | − | +++ | +++ | +++ |
| sucrose fatty acid ester | + | ++ | ++ | ++ |
| sodium dodecylbenzenesulfonate | + | ++ | ++ | ++ |
| sodium n-dodecylbenzenesulfonate | + | ++ | ++ | ++ |
| sodium lauryl sulfate | + | ++ | ++ | ++ |
| higher alcohol sulfuric ester soda | − | +++ | +++ | +++ |

−, +, ++ and +++ indicate the reaction intensities, and the order of the intensities is − < + < ++ < +++.

When dimethyl-β-cyclodextrin as the sugar compound and the protein solubilizing agent are present in the reagent for determining the amount of cholesterol, the amount of HDL cholesterol can be indirectly determined from the amount of cholesterol in LDL, VLDL and CM.

Test Example 3

Using the fractions of HDL, LDL, VLDL and CM which had been fractionated from the serum by ultracentrifugation, the reactivity of each of the lipoproteins with the reagent was measured. In the reagent for determining the amount of cholesterol, 5 mM sugar compound and 5 g/l oxyethylene dodecylamine as the protein solubilizing agent were contained. The results are shown in Table 3.

TABLE 3

| Sugar compound | HDL | LDL | VLDL | CM |
|---|---|---|---|---|
| α-cyclodextrin | ++ | + | + | + |
| β-cyclodextrin | ++ | + | + | + |
| γ-cyclodextrin | ++ | + | + | + |
| dimethyl-β-cyclodextrin | +++ | + | + | + |
| trimethyl-β-cyclodextrin | +++ | + | + | + |
| hydroxyethyl-β-cyclodextrin | ++ | + | + | + |
| 2-hydroxypropyl-α-cyclodextrin | ++ | + | + | + |
| 2-hydroxypropyl-β-cyclodextrin | ++ | + | + | + |
| carboxymethyl-β-cyclodextrin | ++ | + | + | + |
| glucosyl-β-cyclodextrin | ++ | + | + | + |
| maltosyl-α-cyclodextrin | ++ | + | + | + |
| maltosyl-β-cyclodextrin | ++ | + | + | + |
| partially-methyl-β-cyclodextrin | ++ | + | + | + |
| α-cyclodextrin sulfate | ++ | + | + | + |
| β-cyclodextrin sulfate | ++ | + | + | + |

+, ++ and +++ indicate the reaction intensities, and the order of the intensities is + < ++ < +++.

When the sugar compound and 5 g/l oxyethylene dodecylamine as the protein solubilizing agent are present in the reagent for determining the amount of cholesterol, the amount of HDL cholesterol can be directly determined.

Test Example 4

Using the fractions of HDL, LDL, VLDL and CM which had been fractionated from the serum by ultracentrifugation, the reactivity of each of the lipoproteins with the reagent was measured. In the reagent for determining the amount of cholesterol, 5 mM dimethyl-β-cyclodextrin as the sugar compound and 5 g/l protein solubilizing agent were contained. The results are shown in Table 4.

TABLE 4

| Protein solubilizing agent | HDL | LDL | VLDL | CM |
|---|---|---|---|---|
| oxyethylene dodecylamine | +++ | +− | +− | +− |
| polyoxyethylene dodecylamine | ++ | + | + | + |
| polyoxyethylene octadecylamine | ++ | + | + | + |
| sodium cocoylmethyltaurate | ++ | + | + | + |
| sodium lauroylmethyltaurate | ++ | + | + | + |
| sodium myristoylmethyltaurate | ++ | + | + | + |
| sodium palmitoylmethyltaurate | ++ | + | + | + |
| sodium stearoylmethyltaurate | ++ | + | + | + |
| polyoxyethylene lauryl ether | ++ | + | + | + |
| polyoxyethylene cetyl ether | ++ | + | + | + |
| polyoxyethylene stearyl ether | ++ | + | + | + |
| polyoxyethylene oleyl ether | ++ | + | + | + |
| polyoxyethylene behenyl ether | ++ | + | + | + |
| sodium cholate | +++ | + | + | + |
| sodium deoxycholate | +++ | + | + | + |

+−, +, ++ and +++ indicate the reaction intensities, and the order of the intensities is +− < + < ++ < +++.

When dimethyl-β-cyclodextrin as the sugar compound and the protein solubilizing agent are present in the reagent for determining the amount of cholesterol, the amount of HDL cholesterol can be directly determined.

BEST MODE FOR CARRYING OUT THE INVENTION

EXAMPLE 1

Figure 1:
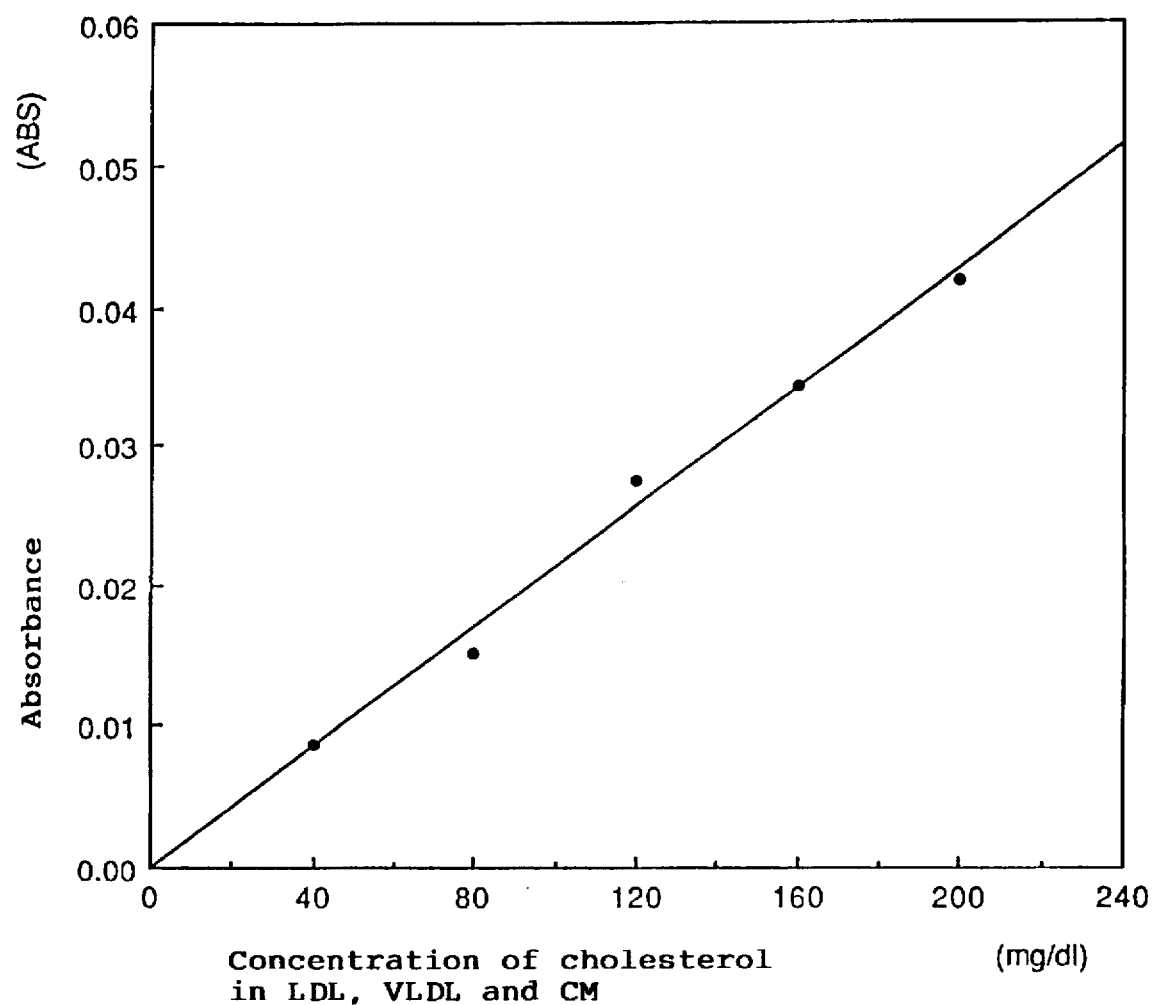
FIG. 1 shows a correlation between the concentration of cholesterol in LDL, VLDL and CM and the absorbance measured by the method of the present invention.

A reagent containing dimethyl-β-cyclodextrin (5 mM), polyoxyethylene laurylamine (5 g/l), cholesterol esterase (1.0 U/ml), cholesterol oxidase (5.0 U/ml), 4-aminoantipyrine (2.2 mM), EMSE (1.1 mM) and 30 mM Good's buffer (pH 6.75) was prepared. A mixed sample of LDL, VLDL and CM which had been fractionated from the serum by ultracentrifugation was used. Three milliliters of the above-mentioned reagent which had been heated at 37° C. were mixed with 50 μl of the sample, and the mixture was reacted at 37° C. for 15 minutes. The absorbance of the obtained solution was measured at 555 nm.

The results are shown in FIG. 1. FIG. 1 indicates a correlation between the amount of cholesterol in LDL, VLDL and CM and the absorbance. The amount of cholesterol in LDL, VLDL and CM was closely correlated with the absorbance.

EXAMPLE 2

Substantially the same procedure as in Example 1 was repeated except that a serum sample was used instead of the mixed sample of LDL, VLDL and CM which had been fractionated from the serum by centrifugation, and the absorbance was measured. The amount of cholesterol in LDL, VLDL and CM in the serum sample was determined on the basis of FIG. 1 and marked as (A). Separately, the total amount of cholesterol in the serum sample was determined using a reagent used in an enzymatic method and marked as (B). The amount of HDL cholesterol was calculated through [(B)−(A)]. As a control, the amount of HDL cholesterol in the serum sample was determined using a dextran sulfuric acid-phosphotungstic acid-Mg precipitation method [precipitation using a Determiner-HDL (manufactured by Kyowa Medex Co., Ltd.)] (Clinical Chemistry, 1st edition, Ogi M., Itensha, p. 110, 1987).

The results according to the method of the present invention were closely correlated with the results according to the precipitation method [coefficient of correlation r=0.832 (n=20)].

EXAMPLE 3

Substantially the same procedure as in Example 2 was repeated except that a reagent containing hydroxyethyl-β-cyclodextrin (10 mM), polyoxyethylene monolaurate (0.5 g/l), cholesterol esterase (1.0 U/ml), cholesterol oxidase (5.0 U/ml), 4-aminoantipyrine (2.2 mM), EMSE (1.1 mM) and 30-mM Good's buffer (pH 6.75) was used instead of the reagent containing dimethyl-β-cyclodextrin (5 mM), polyoxyethylene laurylamine (5 g/l), cholesterol esterase (1.0 U/ml), cholesterol oxidase (5.0 U/ml), 4-aminoantipyrine (2.2 mM), EMSE (1.1 mM) and 30 mM Good's buffer (pH 6.75). The results were compared with the results obtained through the precipitation method.

The results are shown in Table 5.

TABLE 5

| | Concentration of HDL cholesterol (mg/dl) | |
|---|---|---|
| Sample | Method of the present invention | Precipitation method |
| 1 | 49 | 42 |
| 2 | 75 | 68 |
| 3 | 83 | 75 |
| 4 | 53 | 58 |
| 5 | 94 | 96 |

As shown in Table 5, the results according to the present invention were closely correlated with the results according to the precipitation method.

EXAMPLE 4

Substantially the same procedure as in Example 2 was repeated except that a reagent containing dimethyl-β-cyclodextrin (5 mM), cholesterol esterase (1.0 U/ml), cholesterol oxidase (5.0 U/ml), 4-aminoantipyrine (2.2 mM), EMSE (1.1 mM) and 30 mM Good's buffer (pH 6.75) was used instead of the reagent containing dimethyl-β-cyclodextrin (5 mM), polyoxyethylene laurylamine (5 g/l), cholesterol esterase (1.0 U/ml), cholesterol oxidase (5.0 U/ml), 4-aminoantipyrine (2.2 mM), EMSE (1.1 mM) and 30 mM Good's buffer (pH 6.75). The results were compared with the results obtained according to the precipitation method.

The results according to the method of the present invention were closely correlated with the results according to the precipitation method [coefficient of correlation r=0.969 (n=20)].

EXAMPLE 5

A reagent containing dimethyl-β-cyclodextrin (5 mM), oxyethylene dodecylamine (0.25 g/l), cholesterol esterase (1.0 U/ml), cholesterol oxidase (5.0 U/ml), 4-aminoantipyrine (2.2 mM), EMSE (1.1 mM) and 30 mM Good's buffer (pH 6.75) was prepared. HDL sample which had been fractionated from the serum by ultracentrifugation was used. Three milliliters of the above-mentioned reagent which had been heated at 37° C. was mixed with 50 μl of the sample, and the mixture was reacted at 37° C. for 15 minutes. The absorbance of the solution thus obtained was measured at 555 nm.

Figure 2:
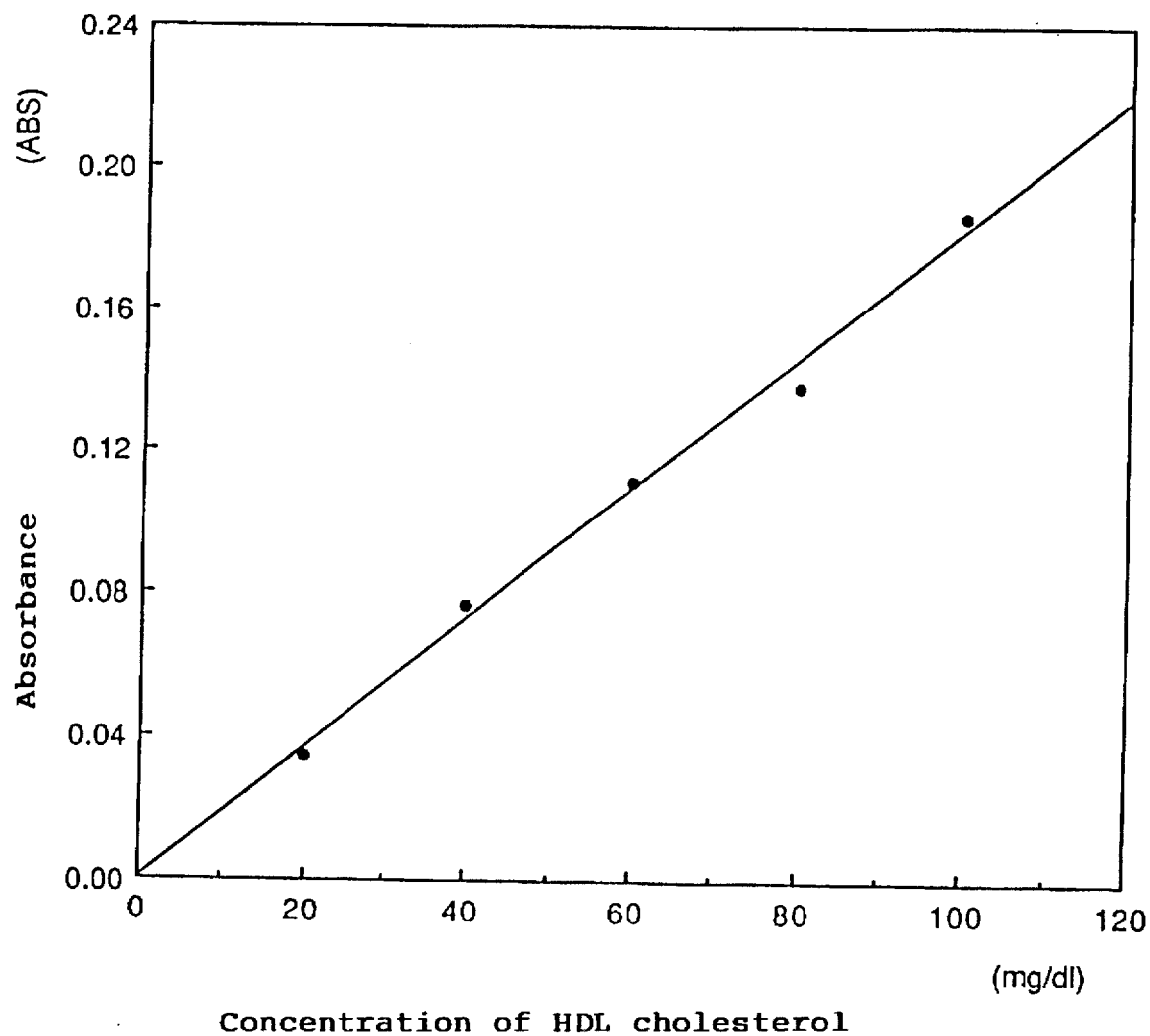
FIG. 2 shows a correlation between the concentration of HDL cholesterol and the absorbance measured by the method of the present invention.

The results are shown in FIG. 2. FIG. 2 indicates a correlation between the amount of HDL cholesterol and the absorbance. The amount of HDL cholesterol was closely correlated with the absorbance.

EXAMPLE 6

Substantially the same procedure as in Example 5 was repeated except that a serum sample was used instead of HDL sample which had been fractionated from the serum by ultracentrifugation, and the absorbance was measured. The amount of HDL cholesterol in the serum sample was determined on the basis of FIG. 2. As a control, the amount of HDL cholesterol in the serum sample was determined using a dextran sulfuric acid-phosphotungstic acid-Mg precipitation method [precipitation using a Determiner-HDL (manufactured by Kyowa Medex Co., Ltd.)] (Clinical Chemistry, 1st edition, Ogi M., Itensha, p. 110, 1987).

The results according to the method of the present invention were closely correlated with the results according to the precipitation method [coefficient of correlation r=0.889 (n=20)].

EXAMPLE 7

Substantially the same procedure as in Example 6 was repeated except that a reagent containing sodium cholate (5 mg/ml), polyethylene glycol-modified cholesterol esterase (1.0 U/ml), polyethylene glycol-modified cholesterol oxidase (5.0 U/ml), 4-aminoantipyrine (2.2 mM), EMSE (1.1 mM) and 30 mM Good's buffer (pH 6.75) was used instead of the reagent containing dimethyl-β-cyclodextrin (5 mM), oxyethylene dodecylamine (0.25 g/l), cholesterol esterase (1.0 U/ml), cholesterol oxidase (5.0 U/ml), 4-aminoantipyrine (2.2 mM), EMSE (1.1 mM) and 30 mM Good's buffer (pH 6.75). The results were compared with the results according to the precipitation method.

The results according to the method of the present invention were closely correlated with the results according to the precipitation method [coefficient of correlation r=0.980 (n=40)].

Industrial Applicability

The present invention provides a simple method of measuring the amount of HDL cholesterol without fractionation step and separation step.

We claim:

1. A method of determining the amount of cholesterol in high-density lipoprotein (HDL), which comprises mixing a sample with a sugar compound and a protein solubilizing agent, measuring the amount of cholesterol in low-density lipoprotein (LDL), very-low-density lipoprotein (VLDL) and chylomicron (CM) in the sample in the presence of the sugar compound and the protein solubilizing agent, and calculating a difference between the amount of cholesterol in LDL, VLDL and CM and the total amount of cholesterol in the sample.

2. A method of determining the amount of cholesterol in HDL, which comprises mixing a sample with a sugar compound and a protein solubilizing agent, and determining the amount of cholesterol in the HDL in the sample in the presence of the sugar compound and the protein solubilizing agent.

3. The method according to claim 1 or 2, wherein the sugar compound is any of a compound represented by formula (I)

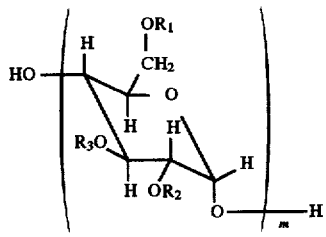
(I)

wherein $R_1$, $R_2$ and $R_3$ independently represents hydrogen, substituted or unsubstituted alkyl, substituted or unsubstituted alkanoyl, sulfo, —(glucosyl)$_p$—H (in which p is 1 or 2) or —(maltosyl)$_q$—H (in which q is 1 or 2), and m is an integer of 6 to 8, and a compound represented by formula (II)

$(C_6H_{10}O_5)_nSO_3R_4$ (II)

wherein $R_4$ represents hydrogen or Na, and n is an integer of 5 to 2,000.

4. The method according to claim 1, wherein the protein solubilizing agent is any of a compound represented by formula (III)

$R_5(CH_2CH_2O)_aH(C_2H_4OOR_6)_b$ (III)

wherein a is an integer of 1 to 200, b is 0 or 1, $R_5$ represents $R_{14}$—X—O— (in which $R_{14}$ represents alkyl or alkenyl and X represents a single bond or CO), or H—(CH$_2$CH$_2$O)$_c$—N($R_{15}$)— (in which c is an integer of 1 to 200 and $R_{15}$ represents alkyl or alkenyl), and $R_6$ represents alkyl or alkenyl, a compound represented by formula (IV)

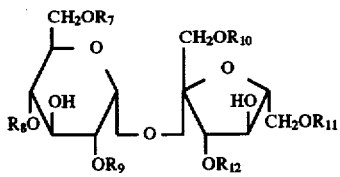
(IV)

wherein $R_7$, $R_8$, $R_9$, $R_{10}$, $R_{11}$ and $R_{12}$ independently represents alkanoyl, and a compound represented by formula (V)

$R_{13}$—Y—SO$_3$Na (V)

wherein $R_{13}$ represents alkyl or alkenyl, and Y represents

—O—, —CH($R_{16}$)— (in which $R_{16}$ represents alkyl or alkenyl), —CH$_2$CH(OH)(CH$_2$)$_d$— (in which d is an integer of 1 to 22), —CH=CH(CH$_2$)$_e$— (in which e is an integer of 1 to 22), —OCOCH(CH$_2$COOR$_{17}$)— (in which $R_{17}$ represents alkyl or alkenyl), or a mixture thereof.

5. The method according to claim 2, wherein the protein solubilizing agent is any of a compound represented by formula (VI)

$R_{18}NHCH_2CH_2OH$ (VI)

wherein $R_{18}$ represents alkyl or alkenyl, a compound represented by formula (VII)

$R_{19}CON(CH_3)CH_2CH_2SO_3Na$ (VII)

wherein $R_{19}$ represents alkyl or alkenyl, and a compound represented by formula (VIII)

$R_{20}O(CH_2CH_2O)_fH$ (VIII)

wherein f is an integer of 1 to 100, and $R_{20}$ represents alkyl or alkenyl.

6. The method according to claim 2, wherein the protein solubilizing agent is a bile acid.

7. The method according to any one of claims 1, 2, 4, 5, or 6, which comprises reacting the sample with cholesterol ester hydrolase and cholesterol oxidase and measuring an amount of hydrogen peroxide formed, wherein the cholesterol ester hydrolase or the cholesterol oxidase used is a chemically modified cholesterol esterase or a chemically modified cholesterol oxidase.

8. The method according to claim 3, which comprises reacting the sample with cholesterol ester hydrolase and cholesterol oxidase and measuring an amount of hydrogen peroxide formed, wherein the cholesterol ester hydrolase or the cholesterol oxidase used is a chemically modified cholesterol esterase or a chemically modified cholesterol oxidase.

* * * * *